(12) United States Patent
Anzalone et al.

(10) Patent No.: US 11,770,586 B1
(45) Date of Patent: Sep. 26, 2023

(54) SYSTEMS AND METHODS OF INTERACTIVE GOAL SETTING TOOLS

(71) Applicant: Wells Fargo Bank, N.A., San Francisco, CA (US)

(72) Inventors: Marjorie S. Anzalone, San Francisco, CA (US); Darius A. Miranda, San Francisco, CA (US); Wairnola Marria Rhodriquez, San Francisco, CA (US); Samundra Timilsina, South San Francisco, CA (US); Paul Vittimberga, Oakland, CA (US)

(73) Assignee: Wells Fargo Bank, N.A., San Francisco, CA (US)

( * ) Notice: Subject to any disclaimer, the term of this patent is extended or adjusted under 35 U.S.C. 154(b) by 0 days.

(21) Appl. No.: 17/882,209

(22) Filed: Aug. 5, 2022

Related U.S. Application Data

(63) Continuation of application No. 16/150,046, filed on Oct. 2, 2018, now Pat. No. 11,412,298.

(51) Int. Cl.
*H04N 21/442* (2011.01)
*G06F 3/01* (2006.01)
(Continued)

(52) U.S. Cl.
CPC ..... *H04N 21/44218* (2013.01); *A61B 5/0205* (2013.01); *A61B 5/165* (2013.01); *G06F 3/011* (2013.01); *G06F 3/012* (2013.01); *G06F 3/14* (2013.01); *G06N 5/04* (2013.01); *G06Q 40/06* (2013.01); *G06V 40/174* (2022.01); *G10L 25/63* (2013.01); *A61B 5/0077* (2013.01); *A61B 5/021* (2013.01); *A61B 5/024* (2013.01); *A61B 5/0533* (2013.01); *A61B 5/0816* (2013.01); *A61B 5/369* (2021.01); *A61B 7/04* (2013.01); *A61B 2503/12* (2013.01); *G06F 3/015* (2013.01); *G06F 3/016* (2013.01); *G06F 2203/011* (2013.01); *G06N 3/126* (2013.01)

(58) Field of Classification Search
None
See application file for complete search history.

(56) References Cited

U.S. PATENT DOCUMENTS 7,894,849 B2   2/2011  Kass et al.
8,560,344 B2  10/2013  Earles et al.
(Continued)

OTHER PUBLICATIONS

"Track all your Goals & Habits in one place", https://www.stridesapp.com/2017. 5 pages.
(Continued)

*Primary Examiner* — Christopher J Fibbi
(74) *Attorney, Agent, or Firm* — Foley & Lardner LLP

(57) ABSTRACT

Examples described herein relate to determining an actual, updated goal of a user based on emotional response data captured while an initial goal is visualized or otherwise perceived by the user, including determining an initial goal of a user, displaying an initial video depicting the initial goal, tracking, with an emotion-tracking device, emotions of the user while the video is displayed by the output circuit by determining emotional response data captured by the emotion-tracking device, updating the initial goal based on the emotional response data to determine an updated goal, and displaying the updated goal.

20 Claims, 6 Drawing Sheets

(51) Int. Cl.
  *G10L 25/63*    (2013.01)
  *G06F 3/14*     (2006.01)
  *A61B 5/16*     (2006.01)
  *A61B 5/0205*   (2006.01)
  *G06N 5/04*     (2023.01)
  *G06V 40/16*    (2022.01)
  *G06Q 40/06*    (2012.01)
  *G06N 3/126*    (2023.01)
  *A61B 7/04*     (2006.01)
  *A61B 5/00*     (2006.01)
  *A61B 5/021*    (2006.01)
  *A61B 5/024*    (2006.01)
  *A61B 5/08*     (2006.01)
  *A61B 5/0533*   (2021.01)
  *A61B 5/369*    (2021.01)

(56) References Cited

U.S. PATENT DOCUMENTS

| | | |
|---|---|---|
| 2002/0073005 A1 | 6/2002 | Welnicki et al. |
| 2003/0135634 A1 | 7/2003 | Moeller et al. |
| 2005/0096973 A1 | 5/2005 | Heyse et al. |
| 2006/0020500 A1 | 1/2006 | Turner |
| 2006/0085217 A1 | 4/2006 | Grace |
| 2009/0096632 A1* | 4/2009 | Ullrich .................. H04N 21/81 340/407.1 |
| 2010/0037170 A1 | 2/2010 | Poole |
| 2010/0107075 A1 | 4/2010 | Hawthorne et al. |
| 2011/0276451 A1* | 11/2011 | Busse .................... G16H 20/70 705/35 |
| 2012/0084372 A1* | 4/2012 | Cohen .................... G06Q 50/01 709/206 |
| 2012/0143693 A1 | 6/2012 | Chung et al. |
| 2014/0134590 A1 | 5/2014 | Hiscock Jr. |
| 2014/0172480 A1 | 6/2014 | Strickholm |
| 2015/0064671 A1 | 3/2015 | Murville et al. |
| 2015/0067708 A1* | 3/2015 | Jensen ............. H04N 21/44218 725/10 |
| 2017/0235830 A1* | 8/2017 | Smith .................... H04L 51/52 707/748 |
| 2017/0293853 A1 | 10/2017 | Chander et al. |
| 2018/0101985 A1* | 4/2018 | Jones-McFadden ... G06V 20/20 |
| 2020/0296480 A1 | 9/2020 | Chappell et al. |

OTHER PUBLICATIONS

Ansaldo, Michael; "The 5 best budgeting apps for tracking and planning your financial life take control of your spending and build wealth", https://www.pcworld.com/article/3093363/data-center-cloud/the-5-best-budgeting-apps-for-tracking-and-planning-your-financial-life.html, Jul. 21, 2016. 7 pages.

* cited by examiner

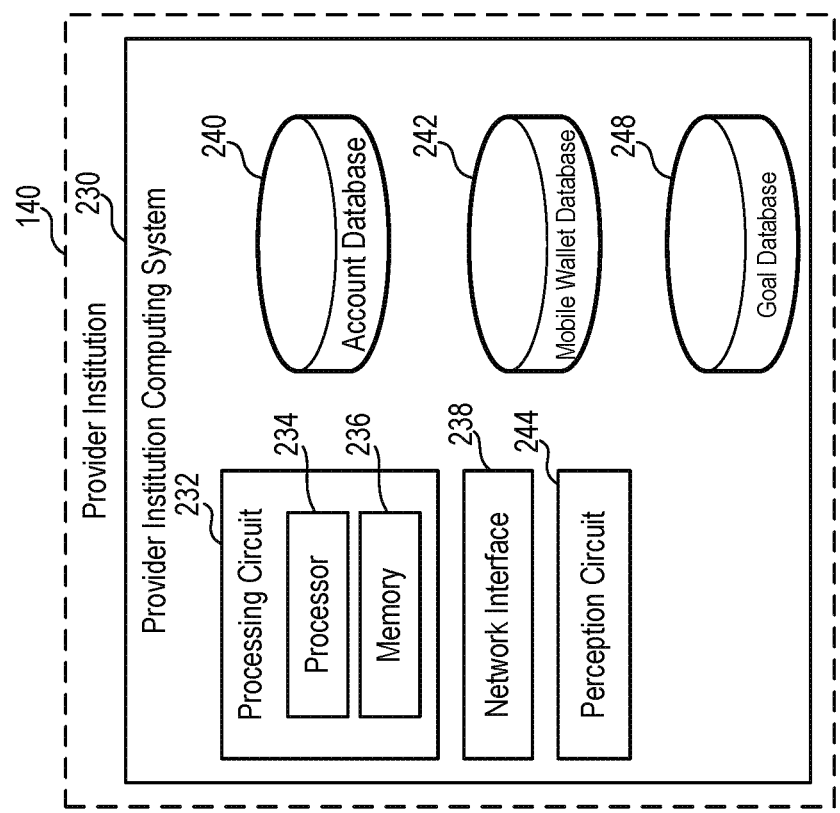
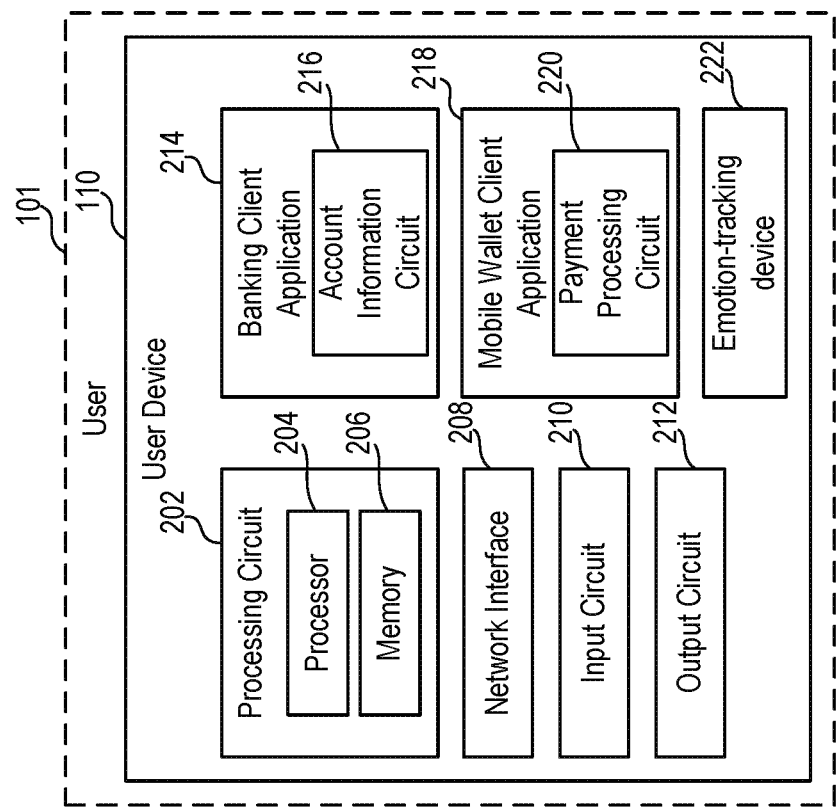

SYSTEMS AND METHODS OF INTERACTIVE GOAL SETTING TOOLS

CROSS REFERENCE TO RELATED APPLICATIONS

This application is a continuation of U.S. patent application Ser. No. 16/150,046, titled "Systems and Methods of Interactive Goal Setting Tools," filed on Oct. 2, 2018, which is incorporated herein by reference in its entirety and for all purposes.

BACKGROUND

Typically, a perceived goal (e.g., a financial goal) of a person corresponds with what the person thinks that the person should be achieving, instead what the person should actually be achieving (e.g., what makes the person happy). Such dissonance may be attributed to human psychology, which makes it difficult for the person himself or herself to distinguish the goals that actually make the user happy from the goals which the user thinks that the user should be achieving.

SUMMARY

In one arrangement, a method for providing goal determination and adjustment includes determining an initial goal of a user of a user device, displaying, with an output circuit of the user device, an initial video depicting the initial goal, tracking, with an emotion-tracking device of the user device, emotions of the user while the initial video is displayed by the output circuit by determining emotional response data captured by the emotion-tracking device, updating the initial goal based on the emotional response data to determine an updated goal, and displaying, with the output circuit, the updated goal.

In one arrangement, a user device configured to provide goal determination and adjustment, the user device includes an output circuit, an emotion-tracking device, and a processing circuit including a processor and a memory. The processing circuit is configured to determine an initial goal of a user of the user device, configure the output circuit to display an initial video depicting the initial goal, configure the emotion-tracking device to track emotions of the user while the video is displayed by the output circuit by configuring the emotion-tracking device to capture emotional response data of the user, update the initial goal based on the emotional response data to determine an updated goal, and configure the output circuit to display the updated goal.

In one arrangement, a non-transitory computer-readable medium having processor-readable instructions stored thereon such that, when executed by a processor, the instructions cause the processor to determine an initial goal of a user of the user device, configure an output circuit of the user device to display an initial video depicting the initial goal, configure the emotion-tracking device to track emotions of the user while the video is displayed by the output circuit by configuring the emotion-tracking device to capture emotional response data of the user, update the initial goal based on the emotional response data to determine an updated goal, and configure the output circuit to display the updated goal.

These and other features, together with the organization and manner of operation thereof, will become apparent from the following detailed description when taken in conjunction with the accompanying drawings.

BRIEF DESCRIPTION OF THE FIGURES

FIG. 2A is a diagram of a user device of the system shown in FIG. 1 according to some arrangements.

FIG. 2B is a diagram of a provider computing system according to some arrangements.

DETAILED DESCRIPTION

Figure 1:
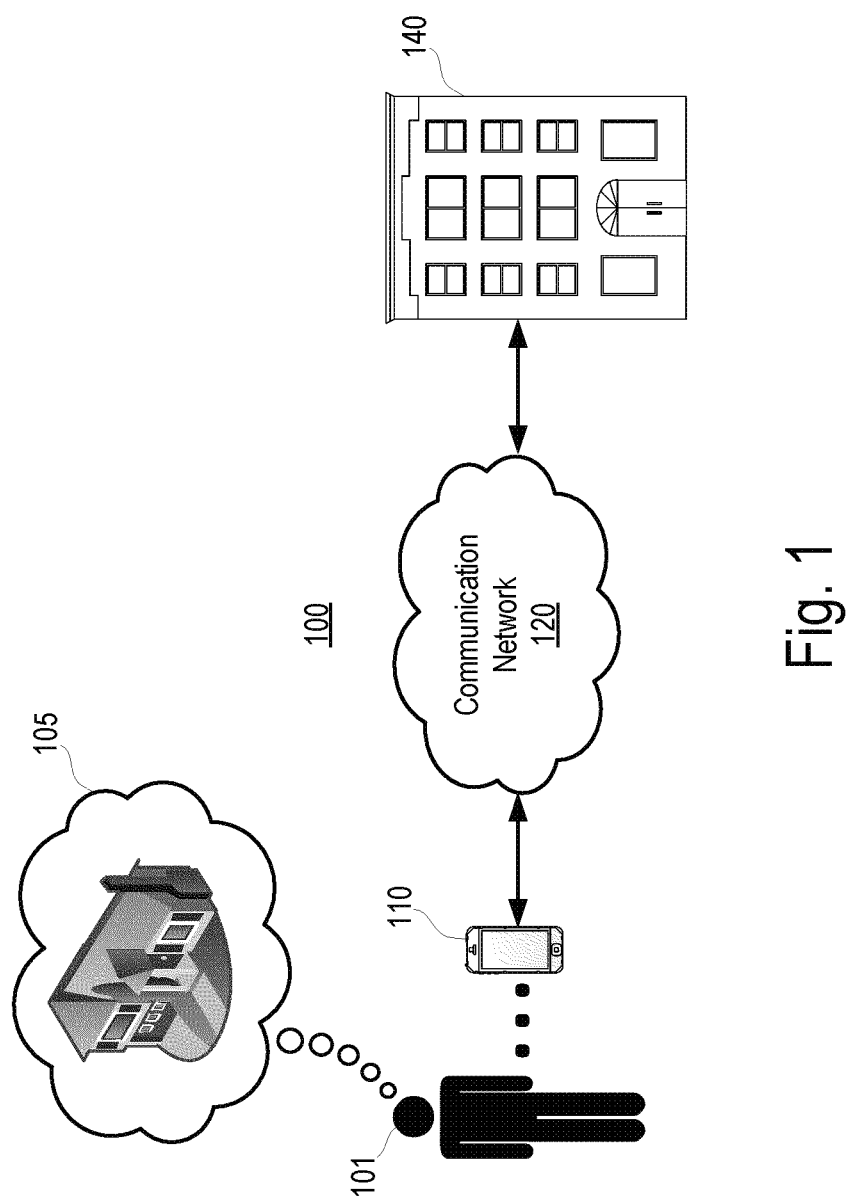
FIG. 1 is a diagram of a system for providing goal determination and adjustment according to some arrangements.

Typically, a conceived goal (e.g., a financial goal) of a person (e.g., a user) is generally aligned with what the user thinks that the user should be achieving, instead of what the user should actually be achieving (e.g., what actually makes the user happy). As such, it is difficult for the user himself or herself to distinguish the goals that actually make the user happy from the goals which the user thinks that the user should be achieving. In addressing such issues, arrangements described herein relate to facilitating the user to identify the goals that actually raise a level of happiness or satisfaction for the user, by leveraging emotional response data collected by an emotion-tracking device (e.g., a camera, a microphone, a heartrate monitor, a breathing rate monitor, a blood pressure monitor, a brainwave analyzer, a skin activity sensor, and so on) of or operatively coupled to a user device, where the emotional response data is collected while the goal is being perceived by the user.

The user device can facilitate visualization or otherwise perception a goal or completion thereof for the user. In some arrangements, the user device (e.g., a smartphone) can be configured to output one or more of visual, auditory, haptic, olfactory information to be perceived by the user. For example, the user device can be configured to display a video or another type of media featuring one or more objects associated with the goal. The visualization or perception of the goal would trigger emotional responses while the goal is being perceived by the user. The emotional responses include explicit emotional responses and implicit emotional responses. Explicit emotional responses include but are not limited to, orally uttered statements, social media posts (e.g., status updates concerning the goal), user input received by the user device, and so on that explicitly express approval or disapproval in connection with the perception of the goal. Implicit emotional responses include facial muscle movements (e.g., smiles, frowns, lip movement, and so on), breathing patterns, oral exclamations (e.g., "WOW!" "NO!" "YES!" and so on), heartrates, blood pressure, brainwave activities, skin activities, and so on. The explicit and implicit emotional responses can be tracked during the visualization or the perception process.

In some arrangements, based on the explicit and implicit emotional responses, the goal (e.g., an initial goal) can be revised or otherwise updated, generating an updated goal. In some arrangements, based on the explicit and implicit emotional responses, recommendations for changes of the initial goal can be determined. The user can select one or more of the recommendations, and the initial goal can be changed in accordance with the selected one of the recommendations. In some arrangements, an updated video can be generated based on the revised or updated goal, to be displayed to the user.

The ability to distinguish the goals that actually make the user happy from the goals which the user thinks that the user should be achieving improve resource allocation by the user, such that the user can allocate more resources toward a goal that actually make the user happy. In general, the arrangements described herein automate goal determination and adjustment that has not been previously automated. The user device, which may be a smart phone, a tablet, other mobile devices, stand-alone computers or the like, includes or is operatively coupled to output capabilities (e.g., screens) to allow the user to perceive the goal as well as emotion-tracking device(s) to determine emotional response data of the user while the user is perceiving the goal. Such a device allows synchronized data collection and correlation between what is being perceived by the user and what is the emotional response of the user, such that the correspondence, especially the temporal correspondence, between the perception (e.g., the video) and the emotion response (e.g., the emotional response data) can be clearly and easily defined.

The arrangements described herein improve computer-related technology and computer functionality of computer-assisted goal determination by performing certain steps that cannot be done by conventional systems or human actors. For example, the system described herein is configured to determine how the user actually feels about a video depicting the goal by assessing the emotional response data captured while the user is watching the video. The system described solves a technical problem on how to automate what would otherwise be a subjective determination of the emotional response of the user. Further, the system described herein can be configured to automatically display an updated goal, which is determined based on the emotional response data. The updated goal may be displayed while the video is being displayed (e.g., the updated goal may be displayed in a pop-up window while the video is playing in the background). Still further, an updated video can be generated based on the updated goal, depicting one or more objects associated with the updated goal. The updated video can be stitched to the initial video such that the videos can be played continuously. In that regard, the video can be updated in real-time. The user's emotional response data can be monitored while the updated video is displayed, to tune the updated goal (if needed). The initial and updated videos being displayed continuously can allow the system to determine the changes to the user's emotional responses, corresponding to the transition from the initial video (corresponding to the initial goal) to the updated video (corresponding to the updated goal). The system can determine another updated goal taking into account the reaction (e.g., the emotional response data captured while the updated video is displayed), and so on. Accordingly, the arrangements described herein allow an iterative process in which a goal of the user is iteratively updated and refined according to the user's reactions to the perception of the goal, and the video being displayed is also iteratively updated (e.g., stitched together) to form a continuous video.

As such, accurate and realistic determination of the goals that actually would fulfill the user can be performed by assessing emotional response of the user to perception (e.g., visualization) of the goals in real-time during a length of a video. A human actor (e.g., a psychiatrist) would not be able to perform such assessment during the length of the video. A human actor needs to observe the user's reactions, often recording the user in a video and re-watching the video to determine the subtle emotional responses of the user. Moreover, a human actor would not be able to generate and stitch updated videos in real-time, in an automatic manner, to continue the iterative process within the context of a continuous video.

In an example arrangement, the system described herein includes a particular and unique set of rules, which are set up to analyze goals of the user, generate videos or other perceptive media for at least one object associated with the goals, assess user responses, and generated updated goals.

FIG. 1 is a diagram of an example of a system 100 for providing goal determination and adjustment according to some arrangements. Referring to FIG. 1, a user 101 can be any suitable entity (e.g., an individual, a company, or the like) whose goal is to be determined and adjusted using the system 100. For example, the user 101 can be a customer or potential customer of a provider institution 140. In some examples, the provider institution 140 is a financial institution providing services to the user. The provider institution 140 can store account information of the user 101, for example, in respective databases 240 and 242 (FIG. 2). While the provider institution 140 is depicted as brick and mortar locations in FIG. 1, one of ordinary skill in the art can appreciate that one or more of the provider institution 140 may not be associated with brick and mortar locations.

The user 101 has one or more goals, represented in FIG. 1 as a goal 105. While the goal 105 is presented as owning/buying a home in FIG. 1, one of ordinary skill in the art can appreciate that the goal 105 can be any suitable goal(s), such as but not limited to, a car, vacation at a beach location in the Caribbean, a college education, engagement ring, and so on. As used herein, the goal 105 of the user 101 refers to a future status reflective of a need or desire of the user 101. In some examples, the goal 105 may be a financial goal. The goal 105 is typically associated with a capability for the user 101 to purchase goods and services in the future. The goal 105 as conceived by the user 101 may be aligned with what the user 101 thinks that the user 101 should be achieving, instead what the user 101 should actually be achieving (e.g., what actually makes the user 101 happy). As such, the goal 105 may be an initial goal that needs to be adjusted in the manner described.

In some arrangements, the user 101 can explicitly state the goal 105 (e.g., the initial goal) via an input circuit (e.g., an input circuit 210 shown in FIG. 2A) of a user device 110, in the manner described herein. In other arrangements, a computing system (e.g., a provider institution computing system 230 of FIG. 2B) can determine the goal 105 (e.g., the initial goal) based on the account information of the user 101 in the manner described.

The user 101 operates the user device 110. The user device 110 is connected to the provider institution 140 (e.g., the provider institution computing system 230 of FIG. 2B) via a communication network 120 to access goods and services provided by the provider institution 140.

The communication network 120 is any suitable Local Area Network (LAN) or Wide Area Network (WAN). For example, the communication network 120 can be supported by Frequency Division Multiple Access (FDMA), Time Division Multiple Access (TDMA), Code Division Multiple Access (CDMA) (particularly, Evolution-Data Optimized (EVDO)), Universal Mobile Telecommunications Systems (UMTS) (particularly, Time Division Synchronous CDMA (TD-SCDMA or TDS), Wideband Code Division Multiple Access (WCDMA), Long Term Evolution (LTE), evolved Multimedia Broadcast Multicast Services (eMBMS), High-Speed Downlink Packet Access (HSDPA), and so on), Universal Terrestrial Radio Access (UTRA), Global System for Mobile Communications (GSM), Code Division Multiple Access 1x Radio Transmission Technology (1x), General Packet Radio Service (GPRS), Personal Communications Service (PCS), 802.11X, ZigBee, Bluetooth, Wi-Fi, any suitable wired network, combinations thereof, and so on. The communication network 120 is structured to permit the exchange of data, values, instructions, messages, and so on among the user device 110 and the provider institution 140.

FIG. 2A is a diagram of an example of the user device 110 of the system 100 set forth in FIG. 1 according to some arrangements. FIG. 2B is a diagram of an example of the provider institution computing system 230 according to some arrangements. Referring to FIGS. 1-2B, the provider institution 140 may include one or more of a bank branch, loan office, mortgage office, services office, retail office, automated teller machine (ATM) location, a combination thereof, and so on. The provider institution 140 has at least one associated provider institution computing system 230. In some examples, the provider institution computing system 230 is a financial institution computing system.

The provider institution 140 provides products and services such as, but not limited to, credit card accounts, mobile wallet, checking/saving accounts, retirement accounts, mortgage accounts, loan accounts, investment and accounts, and so on to the user 101 via the provider institution computing system 230.

The provider institution computing system 230 includes a processing circuit 232 composed of a processor 234 and a memory device 236. The processor 234 can be implemented with a general-purpose processor, an Application Specific Integrated Circuit (ASIC), one or more Field Programmable Gate Arrays (FPGAs), a Digital Signal Processor (DSP), a group of processing components, or other suitable electronic processing components. The memory 236 can be implemented with a Random Access Memory (RAM), Read-Only Memory (ROM), Non-volatile RAM (NVRAM), Flash Memory, hard disk storage, cloud storage, and other suitable electronic storage devices. The memory 236 stores data and/or computer code for facilitating at least some of the various processes described herein. The memory 236 includes tangible, non-transient volatile memory, or non-volatile memory. The memory 236 stores programming logic that, when executed by the processor 234, controls the operations of the provider institution computing system 230. In some arrangements, the processor 234 and the memory 236 form various processing circuits in the provider institution computing system 230.

As shown, the provider institution computing system 230 includes a network interface 238. The network interface 238 is structured for sending and receiving data over the communication network 120 (e.g., to and from the user device 110, another provider institution computing system associated with the provider institution 150, and so on). Accordingly, the network interface 238 includes any of a cellular transceiver (for cellular standards), local wireless network transceiver (for example, 802.11X, ZigBee, Bluetooth, Wi-Fi, or the like), wired network interface, a combination thereof (e.g., both a cellular transceiver and a Bluetooth transceiver), and so on.

The provider institution computing system 230 includes an account database 240 that stores customer information and account information relating to one or more accounts held by the user 101 with the provider institution 140. The account database 240 stores transaction history of transactions made by the user 101 using one or more accounts of the user 101, for example, with a banking client application 214, a mobile wallet client application 218, or with other suitable applications.

The provider institution computing system 230 includes a mobile wallet account database 242 for storing mobile wallet accounts of customers, including the user 101. The mobile wallet accounts permit payments via the mobile wallet client application 218 of the user device 110. The mobile wallet account database 242 stores transaction history of transactions made by the user 101 using the mobile wallet client application 218.

The provider institution computing system 230 includes a perception circuit 244. The perception circuit 244 is configured to determine at least one object corresponding to a goal (an initial goal or one or more updated goals) and generate one or more of visual, auditory, haptic, and olfactory information outputs that allow the user 101 to perceive the goal using the user device 110. For example, in connection with purchasing a suburban home with a two-car garage and five rooms as a goal, the perception circuit 244 can generate an audiovisual output (e.g., a video) depicting an example of a suburban home with a two-car garage and five rooms. In another example, in connection with a vacation at a beach location in the Caribbean, the perception circuit 244 can generate one or more of a haptic output that simulates a sensation of sand, an olfactory output that simulates a smell of a beach, and an audiovisual output (e.g., a video) depicting an example of graphics and sounds of a beach in the Caribbean. The visual, auditory, haptic, olfactory information output generated by the perception circuit 244 can be sent via the communication network 120 to the user device 110, such that the user device 110 can output the visual, auditory, haptic, olfactory information to be perceived by the user 101 in the manner described.

In some examples, the perception circuit 244 is implemented with the processing circuit 232. For example, the perception circuit 244 can be implemented as a software application stored within the memory 236 and executed by the processor 234. Accordingly, such examples can be implemented with minimal or no additional hardware costs. However, other implementations rely on dedicated hardware (e.g., dedicated processor and memory) specifically configured for performing operations of the perception circuit 244.

The provider institution computing system 230 includes a goal database 248 for storing goals (such as but not limited to, the goal 105) of the user (such as but not limited to, the user 101). Upon receiving user-defined goals from the user device 110 or upon determining automatically defined goals, the perception circuit 244 relays the goals to the goal database 248 to be indexed and stored.

As shown, the user 101 operates or is associated with the user device 110. In some arrangements, the user device 110 includes a processing circuit 202 having a processor 204 and memory 206. The processor 204 can be implemented with a general-purpose processor, an ASIC, one or more FPGAs, a DSP, a group of processing components that are distributed over various geographic locations or housed in a single location or device, or other suitable electronic processing components. The memory 206 can be implemented with RAM, NVRAM, ROM, Flash Memory, hard disk storage, and other suitable electronic storage components. The memory 206 stores data and/or computer code for facilitating the various processes described herein. Moreover, the memory 206 is or includes tangible, non-transient volatile memory or non-volatile memory. Accordingly, the memory 206 includes database components, object code components, script components, or any other type of information structure for supporting the various activities and information structures described herein.

The user device 110 is shown to include various circuits and logic for implementing the activities described herein. More particularly, the user device 110 includes one or more of the processing circuit 202, network interface 208, input circuit 210, output circuit 212, the banking client application 214, the mobile wallet client application 218, an emotion-tracking device 222, and so on. While various circuits, interfaces, and logic with particular functionality are shown, it should be understood that the user device 110 includes any number of circuits, interfaces, and logic for facilitating the functions described herein. For example, the activities of multiple circuits are combined as a single circuit and implemented on a same processing circuit (e.g., the processing circuit 202), as additional circuits with additional functionality are included.

The network interface 208 is configured for and structured to establish a communication session via the communication network 120 with the provider institution computing system 230. Accordingly, the network interface 208 is an interface such as, but not limited to, the network interface 238.

One or more of the banking client application 214 and mobile wallet client application 218 are server-based applications executable on the user device 110. In this regard, the user 101 first downloads the application(s) prior to usage. In another arrangement, the banking client application 214 and/or mobile wallet client application 218 are coded into the memory 206 of the user device 110. In still another arrangement, the banking client application 214 and/or mobile wallet client application 218 are web-based interface applications. In this configuration, the user 101 logs onto or otherwise accesses the web-based interface before usage. In this regard, at least one of the banking client application 214 and mobile wallet client application 218 is supported by a separate computing system comprising one or more servers, processors, network interface modules, etc. that transmit the applications for use to the user device 110. In certain arrangements, one or more of the banking client application 214 and/or mobile wallet client application 218 include an API and/or a Software Development Kit (SDK) that facilitate integration of other applications. All such variations and combinations are intended to fall within the spirit and scope of the present disclosure.

The banking client application 214 is communicably coupled to the provider institution computing system 230 (e.g., the account database 240) via the communication network 120 and is structured to permit management of at least one account of the user 101 via the banking client application 214. In this regard, the banking client application 214 provides displays indicative of account information such as, but not limited to, current account balances, pending transactions, profile information (e.g., contact information), reward associated with the account, bill pay information and so on. Further, in some arrangements, the banking client application 214 is configured to process payments from the user 101 to a designated recipient. For example, the banking client application 214 depicts a loan (e.g., mortgage) of the user 101 and allows the user 101 to pay the loan from an account (e.g., checking or savings). In some examples, a bill pay option is provided by the banking client application 214, where the bill pay option allows the user 101 to pay his/her bills in response to user input.

As mentioned herein, via the banking client application 214, the user 101 pays bills (e.g., mortgage), view balances, pays merchants, and otherwise manage accounts. Accordingly and as shown, the mobile bank client application 214 includes an account information circuit 216. The account information circuit 216 is linked or otherwise coupled to one or more accounts (as stored in the account database 240) held by the user 101 and permit management of the associated accounts (e.g., transfer balances between accounts, view payment history) by communicating with the provider institution computing system 230. The banking client application 214 is communicably coupled to the mobile wallet client application 218. As such, in response to a mobile payment via the mobile wallet client application 218, the mobile wallet client application 218 causes the banking client application 214 to update the payment account (i.e., the account that supported the mobile payment). As such, the applications 214 and 218 are communicably coupled to each other to enable actions supported by each respective application.

The mobile wallet client application 218 is communicably coupled to the provider institution computing system 230 (e.g., the mobile wallet database 242) via the communication network 120 and is structured to facilitate purchases by the user 101 via the mobile wallet client application 218. Accordingly, the mobile wallet client application 218 is linked or otherwise connected with one or more accounts (as stored in the account database 240) of the user 101. In operation, when at a point-of-sale terminal, the user 101 initiates the mobile wallet client application 218 and provides a passcode (e.g., biometrics such as a thumbprint, a Personal Identification Number (PIN), a password) to authenticate the user 101 and select the source payment account desired (e.g., a checking account from the provider institution 140 that is linked to the mobile wallet client application 218). Via communication with the payment terminal (e.g., via near field communication), the aforementioned payment information is provided to the POS terminal or the merchant (e.g., via NFC, via barcode presentment) and the payment is processed. Beneficially, carrying payment cards are avoided or reduced via the mobile wallet client application 218.

As mentioned herein, the mobile wallet client application 218 is structured to facilitate and permit payments by interfacing with an account held by the user 101 at the provider institution 140. Accordingly, the mobile wallet client application 218 is communicably coupled via the network interface 208 over the communication network 120 to the provider institution computing system 230. As shown, the mobile wallet client application 218 includes a payment processing circuit 220 structured to facilitate payments by the user 101 via the mobile wallet client application 218. For example, the payment processing circuit 216 enables a quick-pay capability with a merchant. In this regard, the payment processing circuit 216 includes or is communicably coupled with a communication device (e.g., a near-field communication chip) that facilitates the exchange of information between the mobile wallet client application 218 and a POS terminal.

The input circuit 210 is configured to receive user input from the user 101. In particular, the input circuit 210 is configured to receive user input corresponding to user-defined goals (e.g., the initial goal, such as the goal 105). The user-defined goals can be sent to the provider institution computing system 230. The output circuit 212 is configured to output information in the forms of graphics, sound, tactile/haptic feedback, smell, and so on. In this regard, the input circuit 210 and the output circuit 212 are structured to exchange data, communications, instructions, etc. with an input/output component of the user device 110. Accordingly, in some arrangements, the input circuit 210 and the output circuit 212 can be combined into an input/output circuit that includes or is coupled to an input/output circuit such as but not limited to, a display device, touchscreen, keyboard, microphone, and so on. In some arrangements, the input/output circuit includes communication circuitry for facilitating the exchange of data, values, messages, and so on between the input/output circuit and the components of the user device 110. In some arrangements, the input circuit 210 and the output circuit 212 include machine-readable media for facilitating the exchange of information between the input/output circuit and the components of the user device 110. In still another arrangement, the input circuit 210 and the output circuit 212 include any combination of hardware components (e.g., a touchscreen), communication circuitry, and machine-readable media.

The output circuit 212 is configured to output the visual, auditory, haptic, olfactory information output received from the provider institution computing system 230, to allow the user 101 to perceive an initial or updated goal. With respect to visual and auditory information, the output circuit 212 includes one or more suitable screens and one or more suitable speakers for outputting the visual and auditory information. With respect to haptic information, the output circuit 212 includes or is otherwise coupled to haptic gloves or haptic suits configured to generate haptic output when worn by the user 101. With respect to olfactory information, the output circuit 212 includes or is otherwise coupled to an olfactory machine (e.g., digital scent technology or olfactory technology) configured to general olfactory output. Thus, the output circuit 212 can be multi-media and multi-sensory. Examples of the output circuit 212 (as well as the input circuit 210, if the input circuit 210 is coupled to the output circuit 212) include but are not limited to, a virtual reality (VR) device, an augmented reality (AR) device, a smart phone, a tablet, a personal computer, and so on.

In some arrangements, the user device 110 includes an emotion-tracking device 222. The emotion-tracking device 222 is at least one of a camera, a microphone, a heartrate monitor, a breathing rate monitor, a blood pressure monitor, a brainwave analyzer, or a skin activity sensor. The emotion-tracking device 222 is configured to monitor and track emotional responses of the user 101 while the user perceives the initial goal or an updated goal via the output circuit 212.

In some arrangements, instead of the perception circuit 244, the processing circuit 202 of the user device 110 is configured to determine at least one object corresponding to a goal (an initial goal or one or more updated goals) and generate one or more of visual, auditory, haptic, and olfactory information output, based on which the output circuit 212 can generate the corresponding visual, auditory, haptic, and olfactory output to allow the user 101 to perceive the goal.

Figure 3:
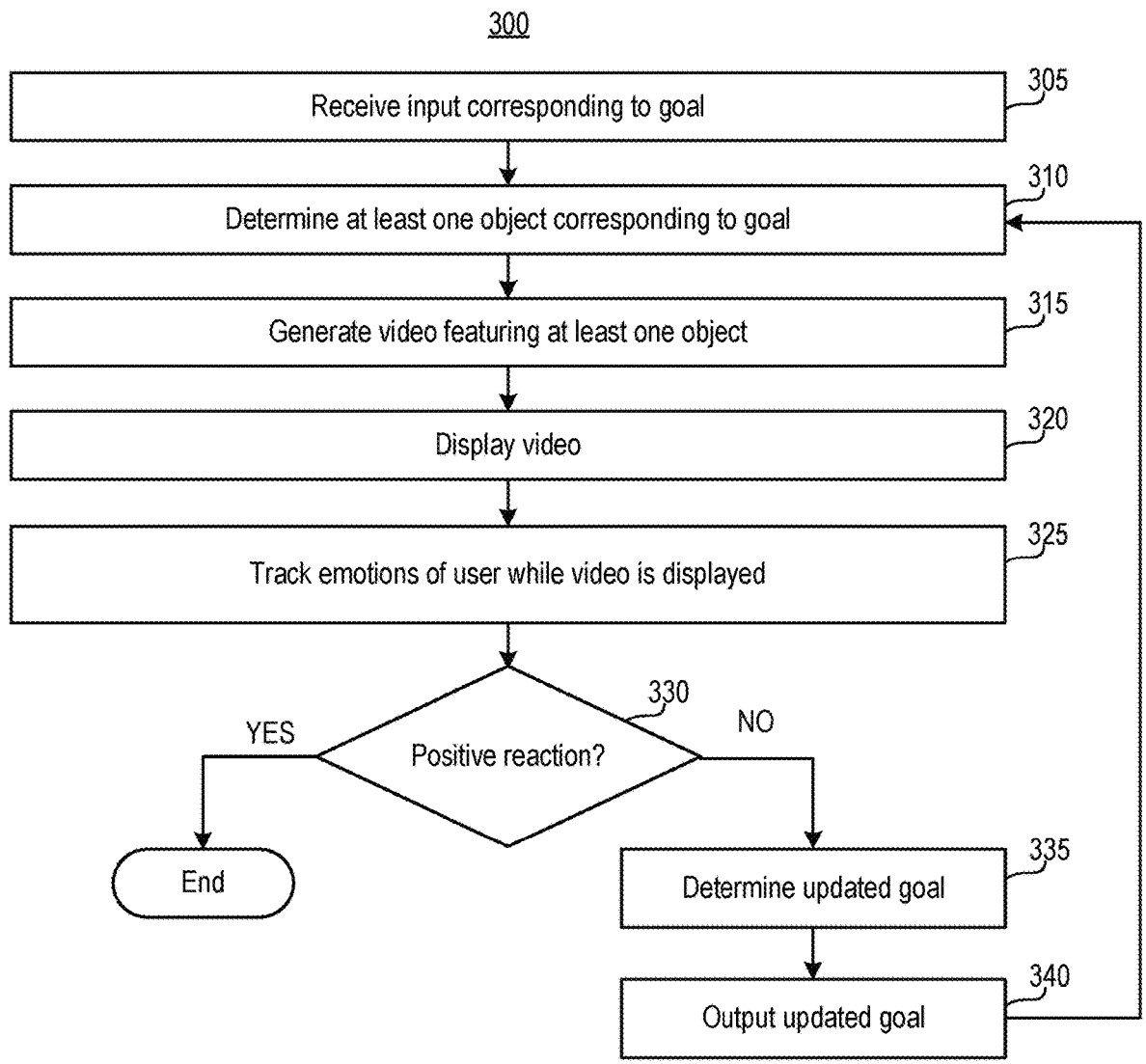
FIG. 3 is a flow diagram illustrating a method for providing goal determination and adjustment according to some arrangements.

FIG. 3 is a flow diagram illustrating a method 300 for providing goal determination and adjustment according to various arrangements. In some arrangements, referring to FIGS. 1-3, the method 300 can be executed by the processing circuit 202 of the user device 110. At 305, input is received corresponding to a goal using the input circuit 210. In some arrangements, the user 101 can define an initial goal (e.g., the goal 105) conceived by the user 101 using the input circuit 210. The initial goal may or may not actually make the user 101 happy. The user input can be received via an application dedicated to the method 300 or via a separate application (e.g., a social media application, a game, or another application that can export the goal to the application dedicated to the method 300). The user input can be received in the form of texts or characters. In some examples, the processing circuit 202 can configure the input circuit 210 and the output circuit 212 to present a "dream board" or a "vision board," which is an interface configured to receive the goal of the user 101.

Alternatively, the goal 105 can be inferred from information of the user 101, including but not limited to, transaction history, inquiries, location data, crowd sourcing, social media, and so on. For example, the processing circuit 232 of the provider institution computing system 230 can be configured to determine from transaction history (stored in the account database 240 and/or the mobile wallet database 242) that the user 101 has purchased an item (e.g., a van). The processing circuit 232 can be configured to identify a goal corresponding to one or more items (e.g., a baby seat) that complement the purchased item. In another example, the processing circuit 232 can be configured to determine from a communication log that the user 101 contacted the provider institution 140 with respect to a product or service (e.g., mortgage) that the user 101 is not currently using. The processing circuit 232 can be configured to identify a goal corresponding to one or more items (e.g., a home) associated with the inquiry. In yet another example, the processing circuit 232 or the processing circuit 202 can be configured to select one or more other users similar to the user 101, for example, using personal identification information (e.g., age, race, gender, nationality, profession, residency, and so on) or purchase history (e.g., the other users purchase similar products and services as the user 101). The information of the other users can be stored in the account database 240, the mobile wallet account database 242, or another suitable database of the provider institution computing system 230 or another suitable system. The goal 105 can be a product or service that the other users have purchased that the user 101 has not yet purchased. In determine what product or service that a user has purchased, the processing circuit 232 or the processing circuit 202 can infer the product or service based on a nature of the merchant with whom the transaction was made. For example, a charge from a commercial transportation company (e.g., an airline, a train operator, a cruise operator, a bus operator, and so on) corresponds to travel. In another example, a large transaction (e.g., exceeding a threshold such as $10,000) with an auto dealership corresponds to purchasing a new automobile. In yet another example, transactions with a hospital/clinic coupled with transactions at store that specialize in infant products correspond to having a baby. In yet another example, the processing circuit 232 or the processing circuit 202 can be configured to determine from location data gathered by the user device 110 that the user 101 (and the user device 110) has visited a location (e.g., a car dealership). The processing circuit 232 or the processing circuit 202 can be configured to identify a goal corresponding to one or more items (e.g., a car) associated with the location. In yet another example, the processing circuit 232 or the processing circuit 202 can be configured to determine from a social media network that connections (e.g., friends, family, colleagues, classmates, and so on) of the user 101 posted about or have achieved the goal.

In some arrangements, the goal 105 inferred from the information of the user 101 can be checked or verified based on financial information (e.g., transaction history) of the user 101 stored in the account database 240, the mobile wallet account database 242, or another suitable database of the provider institution computing system 230 or another suitable system. In other words, responsive to the goal 105 being inferred, the processing circuit 232 can compare the inferred goal 105 against the financial information to which the processing circuit 232 has access. In an example in which the goal 105 is inferred to be "getting married" for the user 101, the processing circuit 232 checks the financial information to determine whether the user 101 has a joint financial account (e.g., a joint checking account, a joint credit card account, a joint investment account, and the like) with a spouse. In addition, the processing circuit 232 can check the financial information (e.g., including information obtained from online forms filled out by the user 101) to determine whether the user 101 is identified to be married as a marital status, whether the user 101 has an online money transfer contact nicknamed "husband" or "wife," whether the user 101 has a beneficiary whose relationship is "spouse." Responsive to determining that the previously inferred goal 105 conforms to the financial information of the user 101, the inferred goal 105 is visualized in the manner described. Responsive to determining that the previously inferred goal 105 fails to conform to the financial information of the user 101, the inferred goal 105 is discarded and another goal 105 is determined.

A monetary value (e.g., how much it costs the user 101 to meet the goal 105) associated with the goal 105 can be determined by the processing circuit 202. In some examples, the monetary value is explicitly defined by the user 101 (e.g., at 305). In an example in which the user 101 defines (with the input circuit 210) the goal 105 to be "saving $X," $X is the monetary value. In other examples in which a monetary value is not explicitly defined with the goal 105, the monetary value can be determined using context information. As used herein, "context information" refers to data associated with the goal 105 and includes data based on which a future monetary value of the goal 105 can be calculated, if the future monetary value of the goal 105 is not explicitly stated. Examples of the context information include but are not limited to, interest rates, market fluctuation, consumer price index, stock market information, location information (e.g., local housing market prices, school district information, local price indexes, and the like), and the like. In particular, the context information can be projected and extrapolated for a stated timeframe (the desired realization time) associated with the goal 105 to determine the future monetary value associated with the goal 105, based on suitable predictive models. Different types of models (e.g., housing market models and stock market models) can be implemented for different types of goals (e.g., buying a home and investing in the stock market, respectively).

At 310, at least one object is determined corresponding to the goal 105. For example, if the goal 105 is "car," "sports car," or "truck," an example depiction of a car, an example depiction of a sports car, or an example depiction of a truck can be determined, respectively. If the goal 105 is "vacation in the Caribbean," an example depiction of one or more of a beach, ocean, beachfront hotel, and so on can be determined. If the goal 105 is "marriage," an example depiction of one or more of a wedding ring, a church, a wedding cake, and so on can be determined. If the goal is "college education," an example depiction of one or more of a dormitory, classroom, books, and so on. If the goal 105 is "saving $X," an example depiction of the monetary value (e.g., $X) in plain text or stylized font can be determined.

At 315, a video featuring the at least one object is generated. In some arrangements, the user device 110 is configured to generate the video. That is, the processing circuit 202 of the user device 110 is configured to generate a video with sounds and graphics corresponding to the example depictions of the at least one object. For example, if the goal is "car," the video shows the example depiction of a car traveling at high speed on a freeway. If the goal is "vacation in the Caribbean," the video shows the example depiction of one or more of the beach, ocean, beachfront hotel, and so on. If the goal is "marriage," the video shows the example depiction of one or more of the wedding ring, the church, the wedding cake, and so on. If the user input is "college education," the video shows the example depiction of one or more of the dormitory, classroom, books, and so on. In some examples, the video generated may include an idealized version of each of the at least one object and the user 101. In other examples, the video generated may include a realistic version of each of the at least one object and the user 101. In some examples, the user 101 may select, via the input circuit 210, the style (idealized or realistic) of the video. In some arrangements, the user 101 may select, via the input circuit 210, a length of the video. The video can be generated to have the length specified by the user 101. In some arrangements, the user 101 may select, via the input circuit 210, a timeline for the video. Examples of the timeline include but are not limited to, past, present, and future. The video can be generated to include elements from the timeline specified by the user 101. For example, a video in the past may feature a younger version of the user 101 (e.g., an image of the user 101 retrieved from social media of the user 101, where the image has been posted from a number of years ago) as well as objects from that era. A video in the present may feature a current version of the user 101 (e.g., an image of the user 101 retrieved from social media of the user 101, where the image has been posted within a predetermined period (e.g., 1 month, 2 months, 6 months, 1 year, or the like)) as well as current objects. A video in the future may feature a future version of the user 101 (e.g., aging an image of the user 101 retrieved from social media of the user 101 to generate an artificially generated older-version of the user 101) as well as objects from the future. A video in the future may feature future results of an achieved goal in the present. For example, an investment that has matured or paid various dividends.

The video can be generated using a template that includes template visual and auditory information. For example, the template may include one or more of an introduction, conclusion, background graphics, background music, and so on. The template may also include designated screen locations configured for displaying the example depictions of the at least one object. That is, the example depictions can be displayed at the designated screen locations, for improved screen space allocation. Thus, the limited space on the screen can be effectively utilized to display as many example depictions for as many goals as possible.

In some arrangements, a context of the video refers to audiovisual contents other than the one or more objects determined for the goal. The context of the video can be determined based on location data collected by the user device 110. For example, whereas the location data of the user device 110 indicates that the user 110 (and the user device 110) is frequently in a certain location (e.g., Napa Valley), then the one or more objects (e.g., a car) can be presented in the video to be at that location (the car is being driven in Napa Valley).

In some examples, instead of a single goal, multiple goals can be defined. Each of the multiple goals can be defined in the manner described. In that regard, at least one object corresponding to each of the goals can be defined. The video features the at least one object corresponding to each of the goals.

Alternative to 310 and 315, the user device 110 is not configured to determine the at least one object corresponding to the goal or generate the video. Instead, the user device 110 is configured to send the user input received at 305 to the provider institution computing system 230, such that the perception circuit 244 is configured to determine the at least one object corresponding to the goal and generate the video in the manner described.

At 320, the video is displayed. In some arrangements, the video is displayed using the output circuit 212 of the user device 110. As described, in addition to the video, the haptic, olfactory information output corresponding to the at least one object in the manner described can be generated. For example, if the goal is "vacation in the Caribbean," haptic information output for a tactile sensation of sand when the user 101 contacts or holds the virtual "sand" while wearing haptic gloves or a haptic suit can be generated. Olfactory information output for a smell of the ocean can be generated. An olfactory machine can generate the smell according to the olfactory information output. The video can be presented as a VR video (via a VR device), an AR video (via an AR device), a 2 D video, a 3 D video (e.g., via the VR device or the AR device), as a photo album, as a storyboard version. In some arrangements, the user 101 can select, via the input circuit 210, an appropriate format for the video.

At 325, the emotions of the user 101 are tracked while the video is displayed. In some arrangements, the user device 110 is configured to track the emotions of the user 101. In some arrangements, emotional response data is captured by an emotion-tracking device 222. Further, the emotions of the user 101 can be tracked while the user 101 is perceiving the goal via the haptic output or olfactory output. The emotional response data can be used to determine whether the user 101 approves or disapproves of the perception of the goal. In some arrangements, the emotional response data can be determined based on user input received while the user 101 is perceiving the goal. For example, the output device 212 is configured by the processing circuit 202 to request user input (e.g., by displaying a question such as "is this what you really want?"). The input device 210 is configured to receive user response, which can be used to determine the emotional response data. In addition, the emotion-tracking device 222 can be at least one of a camera, a microphone, a heartrate monitor, a breathing rate monitor, a blood pressure monitor, a brainwave analyzer, or a skin activity sensor.

A camera can be used to generate videos and photographs of the user 101 while the user 101 is perceiving the goal through the auditory, visual, haptic, and/or olfactory output. Image analysis on features (e.g., the eyes, the eyebrows, the lips, the nose, and so on) of the user 101 can be performed on the videos and photographs to determine the emotional response data (e.g., expression data corresponding to at least one of facial expressions, facial muscle movements, postures, and so on) that are indicative of the emotions of the user 101. The emotions of the user 101 can be used as a proxy for determining whether the user 101 approves or disapproves of the perception of the goal. For example, responsive to determining that the user 101 is smiling while the user 101 is perceiving the goal through the auditory, visual, haptic, and/or olfactory output, it is determined that the user 101 approves of the perception of the goal. On the other hand, responsive to determining that the user 101 is frowning while the user 101 is perceiving the goal through the auditory, visual, haptic, and/or olfactory output, the and frowning, pastures), it is determined that the user 101 disapproves of the perception of the goal.

A microphone can be used to collect emotional response data (e.g., audio data corresponding to sound of the user 101) that is indicative of the emotions of the user 101. The audio data can be analyzed for explicit remarks, speech pattern, breathing rate, and so on to determine whether the user 101 approves or disapproves of the perception of the goal. With respect to explicit remarks, the audio data can be analyzed to identify explicit oral exclamations (e.g., "WOW!" "NO!" "YES!" and so on) that can be categorized as indicative of approval or disapproval. With respect to speech pattern, the audio data can be analyzed to identify raised or lowered voice, speech speed, and so on that can be categorized as indicative of approval or disapproval.

A heartrate monitor can be used to collect emotional response data (e.g., heartrate data of the user 101) that is indicative of the emotions of the user 101. The heartrate data can be analyzed to identify increase or decrease in heartrate and so on to determine whether the user 101 approves or disapproves of the perception of the goal.

A breath rate monitor can be used to collect emotional response data (e.g., breathing data of the user 101) that is indicative of the emotions of the user 101. The breathing data can be analyzed for increase or decrease in breathing rate and so on to determine whether the user 101 approves or disapproves of the perception of the goal.

A blood pressure monitor can be used to collect emotional response data (e.g., blood pressure data of the user 101) that is indicative of the emotions of the user 101. The blood pressure data can be analyzed for increase or decrease in blood pressure and so on to determine whether the user 101 approves or disapproves of the perception of the goal.

A brainwave analyzer can be used to collect emotional response data (e.g., brainwave data of the user 101) that is indicative of the emotions of the user 101. The brainwave data can be analyzed for brain activities (e.g., engagement level, interest level, excitement level, relaxation level, and stress level) and so on to determine whether the user 101 approves or disapproves of the perception of the goal. Examples of the brainwave analyzer include but are not limited to, a Magnetic Resonance Imaging (MRI) machine, an Electroencephalography (EEG) device, and so on.

A skin activity sensor (e.g., an electro-dermal activity (EDA) sensor, a Galvanic skin response sensor) can be used to collect emotional response data (e.g., skin activity data of the user 101) that is indicative of the emotions of the user 101. The skin activity data can be analyzed for skin responses (e.g., changes in skin conductance and sweating) and so on to determine whether the user 101 approves or disapproves of the perception of the goal.

At 330, whether the user 101 is reacting positively to the perception of the goal in the manner described is determined. For example, based on the emotional response data captured by the emotion-tracking device 222, whether the user 101 approves or disapproves of the perception of the goal is determined. Responsive to determining that the user 101 is reacting positively of the goal (330:YES), the method 300 ends. The current goal can be sent to the provider institution computing system 230 to be stored in the goal database 248.

On the other hand, responsive to determining that the user 101 is not reacting positively to the perception of the goal (330:NO), an updated goal based on the emotional response data is determined at 335. In some examples, the processing circuit 202 prompts the output circuit 212 to output a notification indicating that the user 101 is not reacting positively to the perception of the goal and prompts the user 101 to input an updated goal using the input circuit 210.

At 340, the updated goal is outputted. In some arrangements, the output circuit 212 is configured to output the updated goal. For example, the output circuit 212 can display the updated goal to the user 101, while the user 101 is perceiving the goal or after the user 101 has finished perceiving the goal. The method 300 returns to 310, where at least one object corresponding to the (updated) goal is determined.

As such, the method 300 iteratively generates updated auditory, visual, haptic, and/or olfactory output (e.g., an updated video) every time an updated goal is identified. The emotional response data of the user 101 corresponding to the updated auditory, visual, haptic, and/or olfactory output is again analyzed to determine whether the user 101 approves the goal. For example, the processing circuit 202 can generate an updated video based on the updated goal and configures the output circuit 212 to display the updated video. The emotion-tracking device 222 can track emotions of the user 101 while the updated video is displayed by determining the emotional response data captured by the emotion-tracking device 222 in the manner described. Based on the emotional response data captured by the emotion-tracking device 222, the processing circuit 202 can determine whether the user 101 approves or disapproves of the perception of the updated goal (e.g., as shown in the updated video). Responsive to determining that the user 101 is reacting positively of the updated goal, the method 300 ends. On the other hand, responsive to determining that the user 101 is not reacting positively to the perception of the updated goal, the processing circuit 202 can determine another updated goal based on the emotional response data, in the manner described.

In some examples, two videos (e.g., between the initial video and the updated video or between two updated videos) that are displayed sequentially can be stitched together such that the user 101 can perceive the two videos as a single video, even though the two videos are generated at separate times. In that regard, the initial video can be updated in real-time. For instance, the processing circuit 202 can determine a cutoff point for a prior video (e.g., the initial video). The cutoff point can be any time after the determination that the user 101 has not reacted positively to the prior video and before the end of the prior video in some examples. The other examples, the cutoff point is the end of the prior video. The subsequent video (e.g., the updated video), after being generated, can be stitched to the prior video at the cutoff point. In some arrangements, a transition (e.g., fade-out and fade-in) can be provided at the cutoff point. In this manner, the output circuit 212 is configured to play the subsequent video continuously from the prior video. The prior and subsequent videos being displayed continuously can allow the processing circuit 202 to determine the changes to the emotional responses of the user 101 corresponding to the transition from the prior video to the subsequent video. The user 101 is reacting more positively toward the subsequent video indicates that the updated goal is more aligned with what would actually fulfill the user 101, vice versa.

Figure 4:
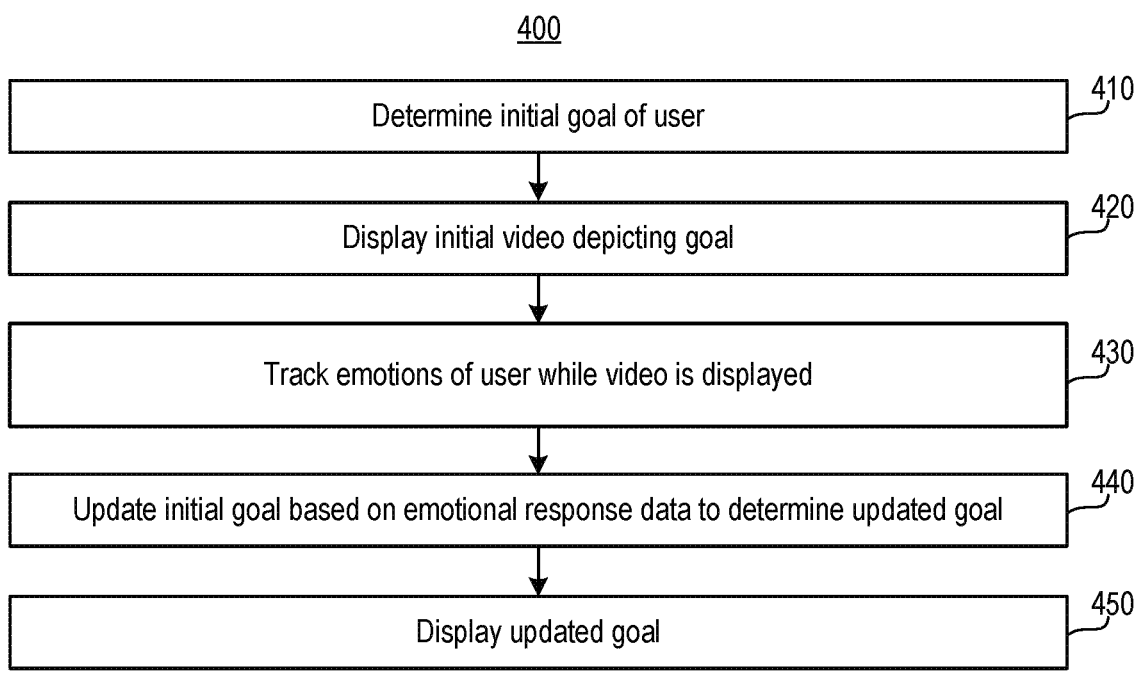
FIG. 4 is a flow diagram illustrating a method for providing goal determination and adjustment according to some arrangements.

FIG. 4 is a flow diagram illustrating a method 400 for providing goal determination and adjustment according to various arrangements. Referring to FIGS. 1-4, one or more blocks of the method 400 corresponds to one or more blocks of the method 300. In some arrangements, the method 400 can be executed by the processing circuit 202 of the user device 110. At 410, an initial goal of the user is determined. At 420, an initial video depicting the initial goal is displayed. In some arrangements, the output circuit 212 is configured to display the initial video depicting the initial goal. At 430, the emotions of the user 101 are tracked while the initial video is displayed. In some arrangements, the emotion-tracking device 222 is configured to track emotions of the user 101 while the initial video is displayed using emotional response data. The emotional response data may be captured by the emotion-tracking device 222. At 440, the initial goal based on the emotional response data is updated to determine an updated goal. At 450, the updated goal is displayed.

In some arrangements, the video can be updated periodically. For example, after the emotional response data is determined while the user 101 is perceiving the goal, the video is not updated in real-time. Instead, the updated video is generated in the manner described at a later time. For example, the updated video can be generated periodically (e.g., within 12 hours, 24 hours, 1 week, 1 month, 1 year, or the like). The updated video can be periodically played to the user 101 after the initial video is displayed. In this manner, the user 101 would have some time to reflect on the goal, and based on the situation, the user 101 may feel differently about the updated goal depicted in the updated video, given that the updated goal is generated based on the emotional response data determined while the user 101 is perceiving the goal when the initial video was being displayed.

Figure 5A:
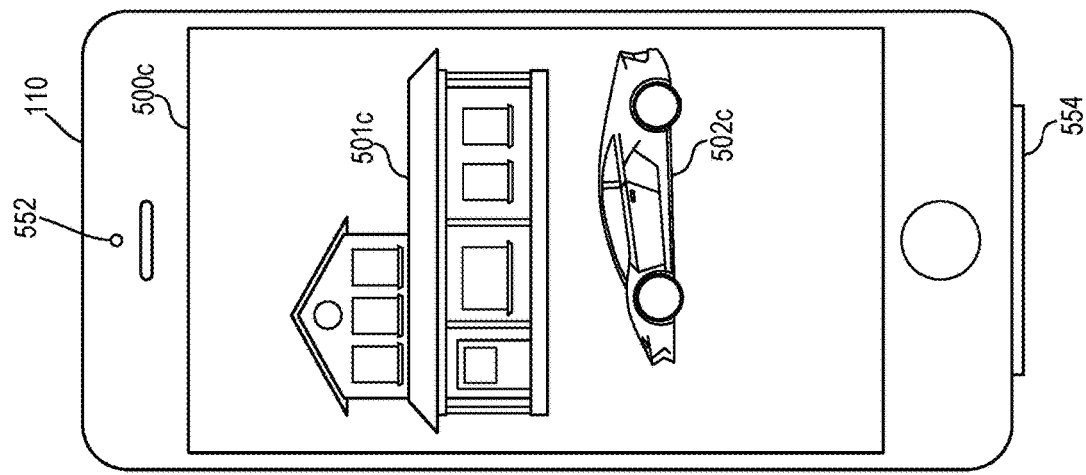
FIGS. 5A-5C are interface display diagrams illustrating interactive interfaces for providing goal determination and adjustment according to some arrangements.
Figure 5B:
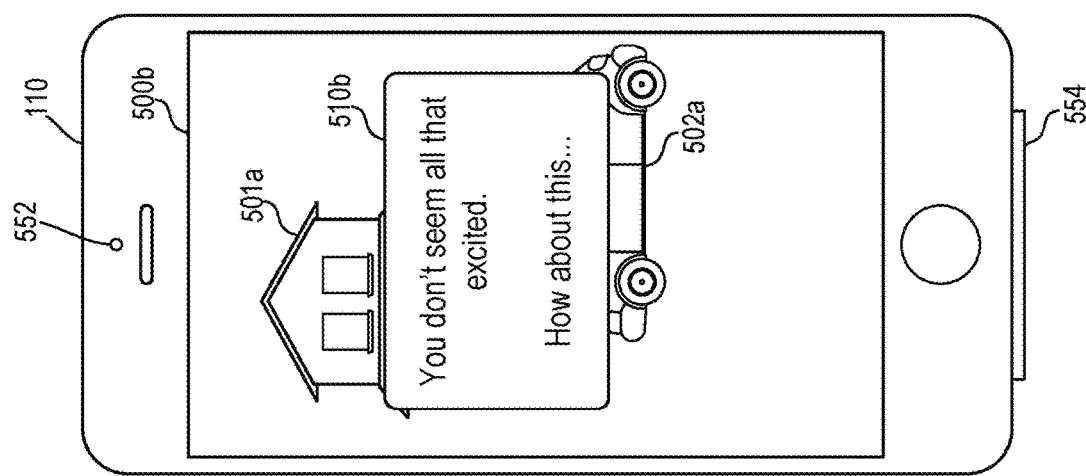
Figure 5C:
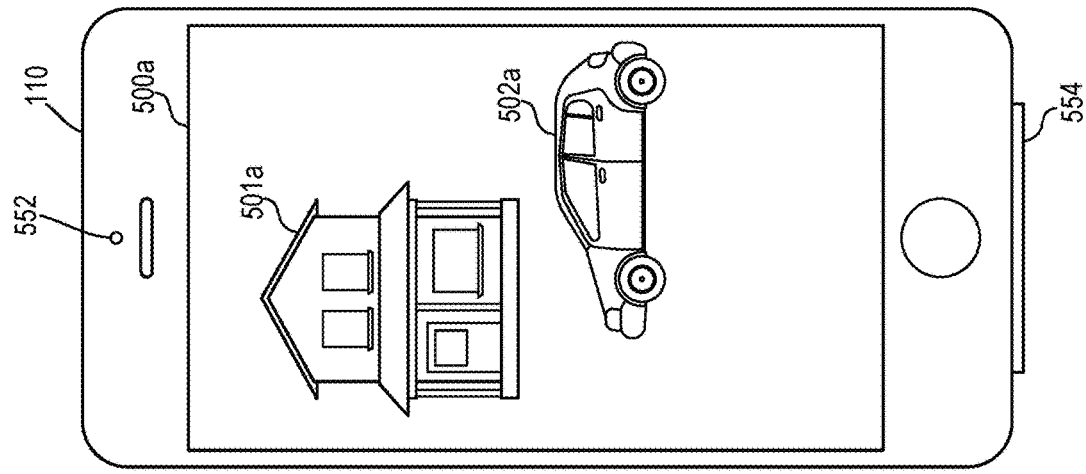

FIGS. 5A-5C are interface display diagrams illustrating interactive interfaces for providing goal determination and adjustment according to some arrangements. Referring to FIGS. 1-5C, the user device 110 is a smart phone and includes a front-facing camera 552 and a microphone 554. The front-facing camera 552 and the microphone 554 are the emotion-tracking devices 222 capable of capturing the emotional response data (e.g., pictures/videos and sound) of the user 101 while the user 101 is perceiving one or more goals through display interfaces 500a-500c displayed via the output circuit 212.

For example, an initial video featuring one or more objects (e.g., a first house 501a and a first car 502a) determined for an initial goal are displayed in the display interface 500a, for example, at 320 or 420. It may be determined that the user 101 is not reacting positively to the video presented in the display interface 500a (e.g., 330:NO). An updated goal may be determined (e.g., at 335 or 440). An updated video corresponding to the updated goal may be generated. In response, a notification 510b, which may be a pop-up window, can be presented in the display interface 500b. The notification 510b can be displayed while the initial video is still playing in the background, or while the initial video is frozen or paused. The notification 510b may notify the user 101 that the updated video is forth coming and/or notify the user 101 of the updated goal. At display interface 500c, the updated video is displayed, featuring one or more objects (e.g., a second house 501c and a second car 502c) determined for the updated goal. In some arrangements, the emotion-tracking device 222 (e.g., the front-facing camera 552 and the microphone 554) can capture the emotional response data of two or more users. In that regard, the emotion-tracking device 222 can track the emotions of multiple users by determining emotional response data of the multiple users captured by the emotion-tracking device 222. In an example in which the emotion-tracking device 222 captures faces of two or more users in images or videos, block 330 is performed with respect to each of the users. In some examples, responsive to determining that one of the users has a negative reaction (330:NO), the method proceeds to 335, even if all the other users exhibit a positive reaction (330:YES). In another example, responsive to determining that a number users that have negative reactions (330:NO) exceeding a threshold (e.g., over 50% of the number of all users), the method proceeds to 335, even if other users exhibit a positive reaction (330:YES).

In some arrangements, the initial video is generated in response to determining that the user 101 has defined a number of goals exceeding a predetermined threshold (e.g., 2, 3, or 5). This ensures that there are enough objects in the initial video to trigger an emotional response.

In some arrangements, a baseline level of happiness is determined for the user 101 immediately before the determination of whether the user 101 is reacting positively at 330. This accounts for the mood of the user 101 affected by events other than the perception of the goal. For example, the processing circuit 202 can scan social media updates of the user 101 to determine the baseline of the user 101. In particular, if the scanning of the social media updates of the user 101 indicates that the user is frustrated, then the determination at 330 weighs the frustration of the user 101 together with the emotional response data determined at 325, to determine whether the user 101 is, indeed, reacting positively or negatively to the perception of the goal.

In some arrangements, the processing circuit 232 can be configured to determine, based on the information stored in the account database 240a and the mobile wallet database 242, that the user 101 has reached a milestone defined and shown in the video. In some arrangements, each of multiple goals presented in the video corresponds to a milestone. For example, if the user 101 defined a goal for buying a home, a goal for buying a van, and a goal for saving an amount of money, the processing circuit 232 can be configured to determine, based on the information in the account database 240a and the mobile wallet database 242, whether those goals or milestones have been achieved. For example, mortgage payments may correspond to achieving the goal of buying a home, car payments may correspond to achieving the goal of buying a car, the user 101 having the amount of money in a particular saving account corresponds to achieve the goal of saving the amount of money, and so on. The processing circuit 232 can be configured to cause a notification to be sent and displayed by the user device 110 (e.g., by the output circuit 212) to notify the user 101 that the user has achieved any one of those goals (milestones). The processing circuit 202 can be configured to cause the output circuit 212 to play the video in which the goals were displayed, identify the object associated with the goal that has been achieved, and play the portion of the video in which the object was shown.

In some arrangements, responsive to or after a momentary value corresponding to the goal 105 is determined, the processing circuit 202 is configured to send the monetary value to the provider institution computing system 230. In some examples, the processing circuit 232 is configured to automatically set up a financial account (e.g., a savings account, an investment account, and so on) for the user 101 (e.g., in the account database 240, the mobile wallet database 242, and so on) to save for the monetary value over time. In some arrangements, Furthermore, the processing circuit 232 is configured to set up automatic transfer that periodically (e.g., monthly, and so on) transfers, from a different financial account of the user 101, a portion of a monthly income (e.g., direct deposit amount or paycheck amount) to the financial account established after or responsive to the monetary value corresponding to the goal 105 being determined.

Figure 6B:
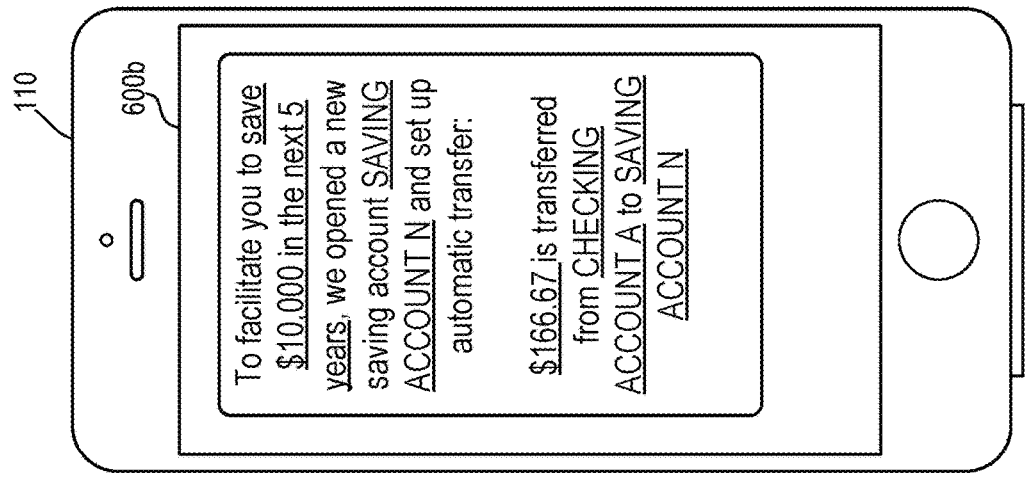
FIG. 6B is an interface display diagram illustrating an interactive interface for automatic account setup according to some arrangements.
Figure 6A:
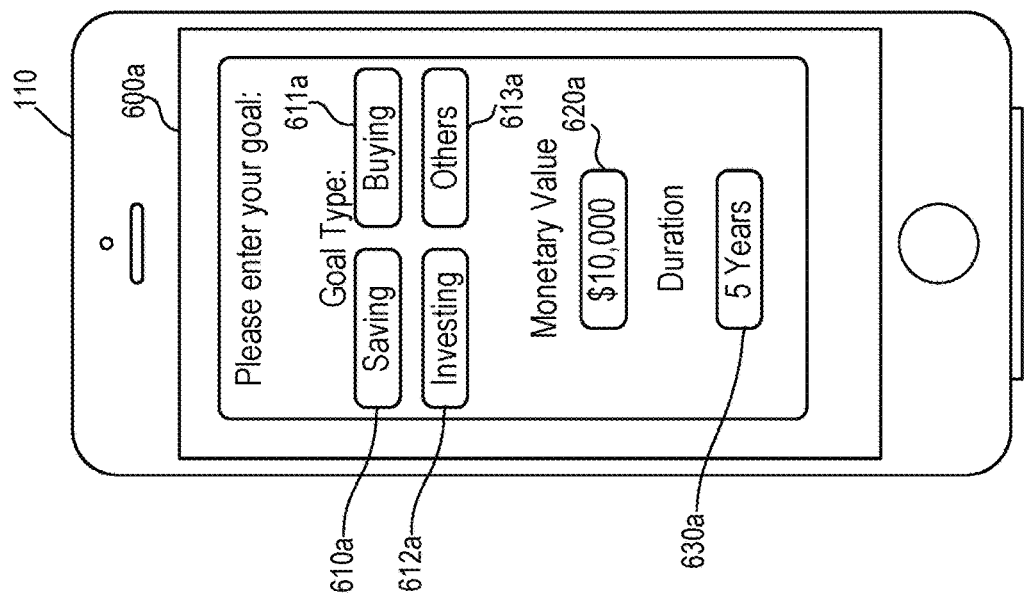
FIG. 6A is an interface display diagram illustrating an interactive interface for goal determination according to some arrangements.

FIG. 6A is an interface display diagram illustrating an interactive interface 600a for goal determination according to some arrangements. FIG. 6B is an interface display diagram illustrating an interactive interface 600b for automatic account setup according to some arrangements. Referring to FIGS. 1-6B, the output circuit 212 is configured to output the display interfaces 600a and 600b.

The interactive interface 600a allows the user 101 to define the goal 105 and to provide a monetary value and realization time associated with the goal 105. For example, the display interface 600a shows user interactive elements 610a-613a corresponding to various goal types. The user 101 selecting user interactive element 610a indicates that the goal 105 corresponds to the user 101 saving a designated amount. The user 101 selecting user interactive element 611a indicates that the goal 105 corresponds to the user 101 buying goods/services. The user 101 selecting user interactive element 612a indicates that the goal 105 corresponds to investments. The user 101 selecting user interactive element 613a indicates that the goal 105 corresponds to subject matter other than saving, buying, and investing. In this example, the user 101 has selected the user interactive element 610a. Responsive to such selection, user interactive elements 620a and 630a may be displayed. The interactive interface 600a further provides the user interactive element 620a configured to receive user input for a monetary value associated with the goal 105 (e.g., saving). In this example, the user 101 has inputted $10,000 as the monetary value (e.g., the user 101 desires to save $10,000). The interactive interface 600a further provides the user interactive element 630a configured to receive user input for an expected realization time for the goal 105. In this example, the user 101 has inputted 5 years as the expected realization time (e.g., the user 101 desires to save $10,000 in 5 years).

The interactive interface 600b is displayed to notify the user 101 that a financial account (e.g., "SAVING ACCOUNT N") has been automatically created for the user 101 to achieve the goal 105 defined using the interactive interface 600a. In some arrangements, responsive to receiving the user input described in connection with the interactive interface 600a, the processing circuit 202 may determine a saving plan to facilitate the user 101 to achieve the goal 105. Here, the processing circuit 202 determines that in order to save $10,000 in 5 years, the user 101 needs to save $166.67 monthly. The banking client application 214 automatically opens a new account (e.g., "SAVING ACCOUNT N") with the provider institution computing system 230, and sets up an automatic payment plan that periodically (e.g., monthly) transfers $166.67 from "CHECKING ACCOUNT A" to "SAVING ACCOUNT N." The interactive interface 600b is used to notify the user 101 of this plan.

Herein, "automatic" is defined as pertaining to an electronically carried out action that does not require outside (either human or machine) intervention to be scheduled, triggered, executed, and/or completed.

The arrangements described herein have been described with reference to drawings. The drawings illustrate certain details of specific arrangements that implement the systems, methods and programs described herein. However, describing the arrangements with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

As used herein, the term "circuit" may include hardware structured to execute the functions described herein. In some arrangements, each respective "circuit" may include machine-readable media for configuring the hardware to execute the functions described herein. The circuit may be embodied as one or more circuitry components including, but not limited to, processing circuitry, network interfaces, peripheral devices, input circuits, output circuits, sensors, etc. In some arrangements, a circuit may take the form of one or more analog circuits, electronic circuits (e.g., integrated circuits (IC), discrete circuits, system on a chip (SOCs) circuits), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR), resistors, multiplexers, registers, capacitors, inductors, diodes, wiring, and so on.

The "circuit" may also include one or more processors communicatively coupled to one or more memory or memory devices. In this regard, the one or more processors may execute instructions stored in the memory or may execute instructions otherwise accessible to the one or more processors. In some arrangements, the one or more processors may be embodied in various ways. The one or more processors may be constructed in a manner sufficient to perform at least the operations described herein. In some arrangements, the one or more processors may be shared by multiple circuits (e.g., circuit A and circuit B may comprise or otherwise share the same processor which, in some example arrangements, may execute instructions stored, or otherwise accessed, via different areas of memory). Alternatively or additionally, the one or more processors may be structured to perform or otherwise execute certain operations independent of one or more co-processors. In other example arrangements, two or more processors may be coupled via a bus to enable independent, parallel, pipelined, or multi-threaded instruction execution. Each processor may be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor), microprocessor, etc. In some arrangements, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system) or remotely (e.g., as part of a remote server such as a cloud based server). To that end, a "circuit" as described herein may include components that are distributed across one or more locations.

An exemplary system for implementing the overall system or portions of the arrangements might include a general purpose computing device in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some arrangements, the non-volatile media may take the form of ROM, flash memory (e.g., flash memory such as NAND, 3 D NAND, NOR, 3 D NOR), EEPROM, MRAM, magnetic storage, hard discs, optical discs, etc. In other arrangements, the volatile storage media may take the form of RAM, TRAM, ZRAM, etc. Combinations of the above are also included within the scope of machine-readable media. In this regard, machine-executable instructions comprise, for example, instructions and data which cause a general purpose computer, special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components), in accordance with the example arrangements described herein.

It should also be noted that the term "input circuits," as described herein, may include any type of input circuit including, but not limited to, a keyboard, a keypad, a mouse, joystick or other input circuits performing a similar function. Comparatively, the term "output circuit," as described herein, may include any type of output circuit including, but not limited to, a computer monitor, printer, facsimile machine, or other output circuits performing a similar function.

Any foregoing references to currency or funds are intended to include fiat currencies, non-fiat currencies (e.g., precious metals), and math-based currencies (often referred to as cryptocurrencies). Examples of math-based currencies include Bitcoin, Litecoin, Dogecoin, and so on.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative arrangements. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and decision steps.

The foregoing description of arrangements has been presented for purposes of illustration and description. It is not intended to be exhaustive or to limit the disclosure to the precise form disclosed, and modifications and variations are possible in light of the above teachings or may be acquired from this disclosure. The arrangements were chosen and described in order to explain the principals of the disclosure and its practical application to enable one skilled in the art to utilize the various arrangements and with various modifications as are suited to the particular use contemplated. Other substitutions, modifications, changes and omissions may be made in the design, operating conditions and arrangement of the arrangements without departing from the scope of the present disclosure as expressed in the appended claims.

What is claimed is:

1. A method, comprising:
displaying, with an output circuit of a user device, an initial video depicting at least one initial object corresponding to an initial goal of a user of the user device, wherein the initial video features the at least one initial object corresponding to the initial goal;
tracking, with an emotion-tracking device of the user device, emotions of the user while the initial video is displayed by determining emotional response data captured by the emotion-tracking device; and
displaying, with the output circuit, an updated video comprising an updated object, wherein the updated object corresponds to an updated goal determined by updating the initial goal based on a baseline and the emotional response data in response to determining that the emotional response data indicates that the user reacted negatively to one or more of the at least one initial objects corresponding to the initial goal, wherein the baseline is determined based on texts inputted by the user.

2. The method of claim 1, wherein the video comprises at least one of a virtual reality (VR), an augmented reality (AR), or a virtual display on the user device.

3. The method of claim 1, wherein the initial goal of the user comprises a goal reflective of a future status of the user's purchasing capability.

4. The method of claim 1, wherein determining the initial goal of the user comprises:
assigning, at least one of a plurality of initial goals, a monetary value determined by context information;
comparing, the monetary value, to financial information of the user; and
determining, if at least one of the plurality of initial goals conform to the financial information of the user.

5. The method of claim 4, wherein if the monetary value of at least one of the plurality of initial goals differs from the financial information of the user, the at least one of the plurality of initial goals is discarded.

6. The method of claim 1, wherein determining the initial object corresponding to at least one of the plurality of initial goals comprises:
determining, by the output circuit, a plurality of depictions that correspond to the initial goal; and
generating, the initial object, based off of at least one of the plurality of depictions.

7. The method of claim 1, wherein the initial goal comprises the plurality of initial goals, wherein determining the at least one initial object corresponding to the initial goal comprises:
determining, at least one initial object corresponding to each of the plurality of initial goals; and
generating the initial video, wherein the initial video features at least one initial object corresponding to at least one of the plurality of initial goals.

8. The method of claim 1, wherein the updated goal comprises a plurality of updated goals, wherein determining the at least one updated object corresponding to the updated goal comprises:
determining, at least one updated object corresponding to each of the plurality of updated goals; and
generating the updated video, wherein the updated video features at least one updated object corresponding to at least one of the plurality of updated goals.

9. The method of claim 1, wherein the initial video is generated using a template and comprises visual and auditory information.

10. The method of claim 1, further comprising:
tracking, with the emotion-tracking device, emotions of the user while the initial video is displayed by the output circuit;
determining, a cutoff point for the initial video;
stitching, the initial video to the updated video at the cutoff point; and
configuring, the output circuit to play the updated video continuously from the initial video.

11. The method of claim 1, wherein the output circuit is configured to play the updated video periodically following the initial video.

12. The method of claim 1, wherein the user's emotional response data is monitored by the emotion-tracking device and the updated goal is tuned according to the emotional response data captured while the initial and updated video is displayed.

13. The method of claim 1, further comprising:
determining, at least one of haptic output or olfactory output corresponding to the at least one initial object; and
outputting, with the output circuit, the at least one of haptic output or olfactory output.

14. The method of claim 1, wherein
the user comprises a plurality of users; and
tracking the emotions of the user while the initial video is displayed comprises tracking emotions of the plurality of users by determining emotional response data of the plurality of users captured by the emotion-tracking device.

15. The method of claim 1, wherein
the user comprises a plurality of users; and
tracking the emotions of the user while the initial video is displayed comprises tracking emotions of the plurality of users by determining emotional response data of the plurality of users captured by the emotion-tracking device.

16. The method of claim 15, further comprising determining the initial goal of the user based off of the initial goal of at least one of the plurality of users with similar financial information.

17. The method of claim 1, wherein the texts inputted by the user is retrieved from a social media application of the user.

18. A user device, comprising:
an output circuit;
an emotion-tracking device; and
a processing circuit comprising a processor and a memory, wherein the processing circuit is configured to:
display, with an output circuit of a user device, an initial video depicting at least one initial object corresponding to an initial goal of a user of the user device, wherein the initial video features the at least one initial object corresponding to the initial goal;

track, with the emotion-tracking device of the user device, emotions of the user while the initial video is displayed by determining emotional response data captured by the emotion-tracking device; and display, with the output circuit, an updated video comprising an updated object, wherein the updated object corresponds to an updated goal determined by updating the initial goal based on a baseline and the emotional response data in response to determining that the emotional response data indicates that the user reacted negatively to one or more of the at least one initial objects corresponding to the initial goal, wherein the baseline is determined based on texts inputted by the user.

19. The user device of claim 18, wherein the user device comprises at least one of a smart phone, a tablet, other mobile device, a stand-alone computer, or other computer devices operatively coupled to output capabilities.

20. A non-transitory computer readable medium of a user device having processor-readable instructions stored thereon such that, when executed by a processor, the instructions cause the processor to:

display, with an output circuit of a user device, an initial video depicting at least one initial object corresponding to an initial goal of a user of the user device, wherein the initial video features the at least one initial object corresponding to the initial goal;

track, with an emotion-tracking device of the user device, emotions of the user while the initial video is displayed by determining emotional response data captured by the emotion-tracking device; and display, with the output circuit, an updated video comprising an updated object, wherein the updated object corresponds to an updated goal determined by updating the initial goal based on a baseline and the emotional response data in response to determining that the emotional response data indicates that the user reacted negatively to one or more of the at least one initial objects corresponding to the initial goal, wherein the baseline is determined based on texts inputted by the user.

\* \* \* \* \*